US008636363B2

(12) United States Patent
Roser

(10) Patent No.: US 8,636,363 B2
(45) Date of Patent: Jan. 28, 2014

(54) INTERACTIVE HOME VISION MONITORING SYSTEMS

(76) Inventor: Mark Costin Roser, Hebron, CT (US)

( * ) Notice: Subject to any disclaimer, the term of this patent is extended or adjusted under 35 U.S.C. 154(b) by 97 days.

(21) Appl. No.: 12/885,964

(22) Filed: Sep. 20, 2010

(65) Prior Publication Data

US 2011/0228227 A1 Sep. 22, 2011

Related U.S. Application Data

(63) Continuation-in-part of application No. 11/803,648, filed on May 15, 2007, now Pat. No. 7,798,645.

(60) Provisional application No. 61/299,554, filed on Jan. 29, 2010.

(51) Int. Cl.
*A61B 3/02* (2006.01)
*A61B 3/00* (2006.01)

(52) U.S. Cl.
USPC ........................... 351/223; 351/239; 351/246

(58) Field of Classification Search
USPC .................................................. 351/200–246
See application file for complete search history.

(56) References Cited

U.S. PATENT DOCUMENTS

| | | | | |
|---|---|---|---|---|
| 5,129,720 A | * | 7/1992 | Jovicevic | 351/243 |
| 5,568,209 A | * | 10/1996 | Priester et al. | 351/243 |
| 5,589,897 A | | 12/1996 | Sinclair | 351/223 |
| 5,844,544 A | * | 12/1998 | Kahn et al. | 345/156 |
| 5,880,814 A | * | 3/1999 | McKnight et al. | 351/239 |
| 6,142,631 A | * | 11/2000 | Murdoch et al. | 351/239 |
| 6,379,007 B1 | | 4/2002 | Farb | 351/239 |
| 7,350,921 B2 | * | 4/2008 | Ridings | 351/237 |

* cited by examiner

*Primary Examiner* — Mohammed Hasan

(57) ABSTRACT

Novel vision monitoring and diagnostic testing tools and help-seeking enablers that may be used individually or in combination as vision monitoring and diagnostic testing systems that improve patients' ability to recognize onset and progression of visual changes over time, so that the identification of acute or chronic visual conditions may be improved and accelerated, which drives earlier help-seeking behavior by the patient, which enables earlier clinical diagnosis by an eye care specialist and therefore earlier treatment and therefore reduced likelihood of severe vision loss.

21 Claims, 8 Drawing Sheets

INTERACTIVE HOME VISION MONITORING SYSTEMS

This application claims the benefit of U.S. Provisional Application Ser. No. 61/299,554 filed Jan. 29, 2010, entitled "Interactive Home Vision Monitoring Systems" and Continuation in Part of U.S. Non-Provisional application Ser. No. 11/803,648, filed May 17, 2007, entitled "Visual & Memory Stimulating Retina Self-Monitoring System" with a projected U.S. Pat. No. 7,798,645 of the same inventor, both of which applications are incorporated herein by reference as to their entire contents.

TECHNICAL FIELD

The technical field relates to vision monitoring and diagnostic testing tools that may be used individually or in combination to create vision monitoring and testing systems that improve patients' ability to recognize visual anomalies as well as the change in vision over time, so that the identification of acute or chronic visual conditions may be improved and accelerated, which may lead to earlier diagnosis by an eye care specialist and therefore earlier treatment and therefore reduced likelihood of severe vision loss.

DEFINITIONS

By the term "affected area"—I mean to describe any type of disturbance to the retina—whether the result of dry macular degeneration, wet macular degeneration, diabetic retinopathy, toxic histoplasmosis, scarring from light or laser, blind spots (scotomas), etc. These words will be used to describe the disturbance in any phase of progression from onset through maturity, pre and post treatment.

By the term "subjectivity of the test"—I mean a lack of ability within the test that would enable consistent measurements over weeks and months of usage.

By the term "lack of quantification"—I mean the lack of patients' ability to remember the extent and shape of a visual distortion or scotoma at a given time.

By the term "anxiety"—I mean that patients who are experiencing visual challenges are under emotional strain and the lack of consistent self-monitoring measurements can exacerbate this state of emotional unrest, and especially a heightened fear of impending blindness.

By the term "doubt"—I mean that patients who are unable to have confidence in the measurement of their vision often don't know whether to attribute a change in their vision to a progression of their disease or consider it within the limits of their test.

By the term "relatively high levels of concentration required"—I mean the lack of proper visual and memory stimulus in Amsler grids places high demands on the patient to maintain concentration to a sufficient level that the patient can observe details in the peripheral visual field, associate these details with a specific location on the grid and then use this information to either communicate with their eye care specialist or compare the results with an earlier grid test result.

By the term "habituation"—I mean that patients using the Amsler grid "get used" to seeing distortions and reduces ability to detect and differentiate changes over longer time intervals.

I will use the terms "earliest stages of disease" and "onset of issues" very loosely and often interchangeably. I will use the terms "adherence", "compliance and "persistence" very loosely and often interchangeably. These terms are used thusly because a general usage does not have a material impact on the nature of the inventions.

By the term "Visual completion phenomenon" (aka the "filling in phenomena")—I mean that the brain working together with the eyes is able to fill-in and approximate areas of missing vision and thus makes proper visualization of the size and shape of an affected area of the visual field (such as a scotoma) difficult, less accurate and less able to track over months & years of time.

By the term "eye care specialist"—I mean a health care practitioner that may include a variety of disciplines comprising opticians, eye care technicians, staff of eye doctors, optometrists, ophthalmologist, retina specialists—that may either diagnose and treat or refer patients so that they may get to a doctor that will diagnose and treat.

By the term "vision test" I include reference to both vision monitoring and vision diagnostic testing tools.

By the term "absolute vision measurement" I refer to a vision test which provides results that may be evaluated against an accepted clinical standard. For example in the field of acuity measurement, an absolute vision measurement may provide a measurement of near vision acuity as determined by standards such as Snellen, LogMar, M-Units, Jaeger Equivalents, etc. And may lead to a clinical measurement such as "20/20".

By the term "relative vision measurement" I refer to a vision test which may produce outcomes that may be evaluated for a specific user when executed at different times. The test is not dependent upon a standard or clinical reference point. It holds value in its ability to detect changes over time. For example in the field of acuity measurement, a relative vision measurement provides a specific user the ability to compare the result garnered at a given time with the result garnered at a different point in time and thereby evaluate any change between the two readings.

By the term "baseline" I refer to an activity whereby a user conducts a test or set of tests to establish an absolute or relative vision measurement. The dates of the test or set of tests often are associated with a user's visit to their doctor, where an absolute vision measurement has been establish and documented in a clinical setting.

By the term "baseline results" I refer to documented measurements associated with a user's performance in an absolute or relative vision measurement or set of measurements. A set of baseline results are associated with a specific type of test, for example, a near vision acuity test that uses individual capital letters in groups of 5 arranged in rows. Baseline results provide the ability for an individual user to establish a fixed set of results for a specific vision test against which the same user taking the same test may compare subsequent absolute or relative vision measurements.

By the term "baseline heuristics" I refer to a calculated range of measurements that document a range of performance in an absolute or relative vision measurement or set of measurements. More specifically, to interactive vision tests which may produce a range of outcomes depending upon non-vision-related variables such as alertness, cognition, dexterity, consistency, etc. Baseline heuristics enable the gathering of performance results for multiple measurements of the same test by the same user over a limited time period. For example, the first 3 results of a given user for a specific test. The heuristics may then be used in statistical calculations to establish high and low boundary levels that will determine whether future test results indicate normal vision or a possible change in vision. For example, a user playing a vision testing game in electronic or paper based format may record the results of their first 4 uses of a given test, take a numerical weighted average of the results and set a lower bound of 90% and upper bound of 110%, such that if future results fall outside of this range, the user may be alerted to a possible change in vision.

By the term "same sized characters" I refer to characters of the same basic height. If the characters were letters or number, they would typically be part of the same font size and family. Same sized characters may comprise capitalized letters, also known as upper case letters, lower case letters, picto-gram symbols, pictorial, numbers, or directionally oriented objects. By pictorial and picto-gram, I refer to use of graphical icons and small silhouettes to provide a visual identification. Such items may be marked by any number of means, comprising a circle, x-mark, underscore, highlight and hashmark. By hash mark, I refer to a single or double stroke through a symbol to provide a marking.

By the term "line of same sized characters" I refer to a vertical column or horizontal row of similar sized characters.

BACKGROUND OF THE INVENTION

Description of the Unmet Need

Vision loss is disruptive to the individual affected, their family and society. There are many causes of vision loss and vision impairment. Many of these conditions are treatable.

Age-related macular degeneration (AMD) is a leading cause of irreversible legal blindness in the western world. Over 12 million Americans have some type of AMD, and millions of others suffer from other retina issues. Current home self-monitoring tools for retina diseases fail to adequately indicate a change in vision, resulting in delayed treatment starts and higher incidences of severe vision loss.

Other ophthalmic conditions ranging from refractive error to cataracts to glaucoma also respond to intervention. Unfortunately, many people affected by these disorders suffer needlessly because they are either unaware of their condition or they do not respond to their symptoms with sufficient promptness. This often leads to a delay in presentation after the onset of a visual change, which creates a delay in clinical diagnosis and therefore a delay in the start of treatment, which may lead to permanent and unrecoverable vision loss.

The novel concepts described herein boost patients' ability to accurately and confidently self-monitor their vision in a home environment, which enables improved recognition of symptoms, which drives proper help-seeking behavior, which enables acceleration of presentation to an eye care specialist, which enables earlier clinical diagnosis of onset or progression of disease, which enables earlier start of treatments, which leads to fewer people losing vision.

The Amsler and Yanuzzi grids, the only widely used self-tests for AMD, have proven largely ineffective at enabling patients to recognize the signs that they should consult their retina specialist for treatment. There are no other commonly available tools for patient self-monitoring in one's home between office visits. The Amsler Grid has been in use and largely unchanged for more than 60 years. Shortcomings of the Amsler grid include but are not limited to: periodicity of the test pattern, lack of individual adjustment, lack of visual & memory stimulating triggers, inability to overcome the visual completion phenomenon, poor compliance, subjectivity, lack of quantification, anxiety and doubt, relatively high levels of concentration required and habituation.

With respect to refractive error, cataracts, glaucoma and other vision disorders, a good assortment of educational literature and information is available from doctors as well as over the Internet. However, the problem of late presentation persists and it is evident that there is a gap in the marketplace for novel solutions that deliver educational messages and self-monitoring tools that can help accelerate patient presentation for all forms of vision loss.

While the dry form of AMD progresses slowly over years, the wet form of AMD progresses rapidly and can mature from a nascent stage to legal blindness in fewer than 12 months. Studies have shown that typical wet AMD patients can take 6 months to present after the onset of symptoms. Thus, annual vision check-ups are not sufficient to protect patient's visual health; and diligent home self-monitoring is essential. However, the current grid tests do not provide effective self-monitoring. The result is that many people are needlessly suffering advanced vision loss and blindness because they lack the ability to accurately and confidently monitor their vision and know when to accelerate their visit to their eye care professional before their scheduled appointment date. By waiting until their routinely scheduled exam date or not presenting until vision loss impacts activities of daily living, people put their visual health at risk.

Studies have also shown that anti-VegF treatments for wet AMD are more effective the earlier they are started. Earlier presentation, therefore leads to lower initial vision loss, improved therapeutic outcomes and a greater likelihood of maintaining or restoring remaining vision. Each day that a patient delays the start of treatment may lead to worsening and often irreversible loss of vision.

In clinical testing, the Amsler grid has not proven successful at enabling patients to detect issues nor to understand when to seek council of their retina specialist. The following references are made to the scientific literature:

Referencing: Schuchard, Arch. Ophthalm 1993 vol 111 no. 6

"For scotomas of 6 degrees or less in diameter, 77% of standard and 87% of threshold scotomas were not detected by Amsler grid testing." "Amsler Grid reports have poor validity and cannot be accurately interpreted for use in the clinical diagnosis of retinal defects."

Zaidi, et al, Eye, May, 2004

"The surveillance protocol detected less than 30% of the specific patients who subsequently underwent laser treatment." "Bearing in mind the prevalence of AMD and the increased therapeutic importance of early detection of SRN, it is clear that improvements in the current surveillance protocol are required."

Achard, et al, Am J Ophthalmol. 1995

"Results of two successive Amsler grid tests were not comparable, even when the technique was identical and time between tests was no more than 2 to 15 min." "the Amsler grid technique is unreliable for evaluating central scotomas."

A variety of reasons have been put forward by these studies to explain the reasons behind the poor performance of the Amsler grid:

Schuchard, Arch. Ophthalm 1993 vol 111 no. 6

"The perceptual filling-in of patterns such as the Amsler grid and fixation characteristics have a major influence in the result of Amsler grid testing."

Zaidi, et al, Eye, May, 2004

" . . . difficulty with compliance . . . ", " . . . problems with the subjective nature of the test.", "Relatively high levels of concentration are needed to undertake the test . . . ", " . . . levels of fatigue and anxiety are important,", " . . . compounded by the perceptual completion phenomenon . . . "

Achard, et al, Am J Ophthalmol. 1995

"Our data corroborated Schuchard's observations regarding the relatively poor sensitivity of Amsler grid tests.", "Additionally, our study further characterized the completion phenomenon found when Amsler grid tests are used and emphasized the rapid changes that occur in completion over time.", "It cannot be excluded that the changes in results over time were partly because of changes in fixation position."

This research is corroborated by the inventor's general conversation with retina patients. In interviews, the following assertions regarding the Amsler are supported by patient observations:
1. Poor compliance with test protocol—many neglect to do any testing
2. Confusion regarding purpose—many did not know why they were given the Amsler
3. Confusion regarding baseline & monitoring—none knew they were supposed to monitor their vision over time
4. Confusion regarding proper usage—several reported looking for "moving" or "changing" lines as if they expected to see motion on the card as the symptom of further disease Patients delay for multiple reasons. Many patients are simply unaware of the onset of a problem; this frequently occurs when the onset occurs in the non-dominant eye or in patients with a high degree of blur tolerance. Many patients are aware of their symptoms but don't have confidence in their self assessment to consider the changes to be significant; this leads them to question whether their vision is truly different than it was last week or the week prior allowing slow progression of vision loss to continue without triggering a help-seeking response. Many patients are aware of their symptoms and have confidence in their self-assessment but incorrectly attribute the problem to a less severe cause such as simply needing new glasses or the progression of cataracts. Many patients are aware of their symptoms and have confidence in their self-assessment but do not respond with urgency, perhaps hoping vision will restore itself and simply waiting until their next scheduled eye exam to discuss the anomaly with their doctor; this can lead to situations where patient's inability to make a decision about seeking help wait until a dire consequence of functional blindness before they feel the urgency to decide to seek help. Many patients delay out of an inability to arrange an appointment with an eye doctor, either because of transportation issues, inability to master reimbursement questions, the need to attend to higher morbidity diseases, lack of a relationship with an eye care specialist, and others.

Lack of confidence in self assessment can frequently be attributed to shortcomings in the standard of care in home vision monitoring—the Amsler grid. In the inventor's personal experience as a wet AMD patient for over 10 years, the Amsler grid has shortcomings in further areas, including but not limited to:
1. Difficulty in detecting changes to vision especially subtle changes
2. Difficulty in locating the periphery of the affected, scarred or damaged retinal area
3. Difficulty in detecting changes to the size or complexion of an affected area
4. Difficulty in establishing a benchmark viewing distance
5. Difficulty in locating and/or maintaining a gaze at the center of a grid without wandering
6. Difficulty in remembering the exact limits of an affected area The impact of these diagnostic shortcomings include but are not limited to:
1. Substandard identification of newly affected areas (of the retina)
2. Incorrect or missing identification of newly affected areas
3. Substandard assessment of size and complexion of affected areas
4. Lack of confidence in daily measuring
5. Frustration with the assessment process
6. Variation in day-to-day assessment of the overall size and complexion of an affected area
7. Anxiety regarding uncertainty of whether the vision loss is getting better or worse The consequences of these impacts can lead to (but are not limited to) unnecessary delays in presenting to an eye care professional.

The implication to the eye care industry are many:
1. Fewer patients receive intervention at the earliest stages of disease (drug therapy, corrective lenswear, surgery, etc)
2. Fewer patients fall within the treatable range of the disease because many have progressed beyond acceptable treatable limits for first-line therapies, reducing the armamentaria available to the treating physician
3. More patients fail to receive full benefit of their treatment, some find the treatment ineffective because they started late, and many lose significant vision
4. Certain therapies that are used in late-presenting patients may not establish optimal health outcomes if compared to a scenario where more patients presented days or weeks earlier Societal implications include, but are not limited to:
1. Vision loss directly reduces a patient's ability to be a productive contributor to society
2. Vision loss indirectly taps patient's family's ability to productively contribute to society
3. Vision loss increases the need for social services and other governmental support
4. Delayed presentation increases the extent of treatment required, increasing the monetary costs through public & private insurance programs The novel ideas and approaches enclosed will benefit others by giving them more accuracy, simplicity and ease in the monitoring of their vision. As a result, monitoring will be performed more regularly, with better adherence and higher accuracy and confidence. And thus, any necessary treatments will be delivered as soon as practical thereby increasing the chances for best treatment results and reducing the risk of vision loss and blindness.

Background Info—the Use of Acuity Testing such as Near Vision Acuity Testing

In traditional vision care, an eye care professional will measure near vision acuity in the exam room with a small semi-rigid card with printed indicia comprising the test characters. The patient will hold the test and read the content of the test to their best ability. Many acuity tests, such as the near-vision Snellen have a series of letters or symbols with common character size on each row. Each consecutive row has a smaller font size. By maintaining a consistent distance between the eye and the test and knowing the size of the characters used, one can get an indication of near vision acuity for each eye. Use of standardized sized characters at a measured distance in a properly lit area allows for absolute vision measurement and a clinical diagnosis of acuity.

When testing near vision acuity, the eye care professional may measure the distance between the test and the patient's eyes, or there may be a string attached to the test to enable the patient to hold the test at a fixed distance.

In a home environment, a critical measure of the effectiveness of any tool is the patient's ability to adhere to a testing regimen over multiple years. A home testing system loses its value when patients stop using it. Few patients have the patience to measure the distance between their test and their eyes each time they use a test. Samples of patients who have been interviewed have stated that they find use of a string to maintain proper distance as being cumbersome. A trade-off exists regarding whether to force patients to measure or maintain precise distance between the test and the eyes and risk poor compliance, or to allow patients to use a test without use of distance tools and hope to maintain compliance over many years.

Novelty within the system herein recognizes this trade-off and does not request patients to measure the vision between their eyes and the test or request patients to use a string to maintain a fixed distance.

In observing patients, especially those over 60, one can recognize that the effects of presbyopia have rendered most people with a narrow band of distance between the eyes and the reading article where acuity is optimal. Patients often extend the reach of their arms to help enable them to focus on small print. The lens of the eye loses flexibility with age, and patients are thus left with only a narrow range of distance that is usable for reading fine print.

When reading fine print—as with a near vision acuity test's lower limits, patients, especially those over 60, have a limited range of distance where they hold their reading materials. After a patient has reached their 60's, this range of distance does not vary greatly from year to year. This distance will vary from patient to patient and with the nature of corrective lens-wear selected. Thus, while this distance may not easily facilitate an absolute measure of vision, its consistency week over week is sufficient for conducting relative vision measurements.

For patients who are able to read fine print at a variety of distances, tests can include a component that alerts people that a change in distance (bringing the test closer to the eyes) is also a symptom of acuity loss. Thus, the instructions to patients can alert them that a change in acuity may be detected by either a significant change in the character size that can be read and a significant change in the distance used to hold the test object. This enables relative vision monitoring when using near vision acuity tests with variability of reading distance between three and thirty inches between the test characters and the user's eyes. Thus a change in reading distance becomes the determination of vision change.

In a clinical setting, once the near vision acuity test is completed, the acuity testing device is subsequently handed back to the eye care professional and maintained as part of the office equipment. Results of the test are documented in the patient's chart. The patient is not provided with any facility to observe or monitor their acuity between office visits. The patient's acuity is used as a pure clinical measure and not typically as a home monitoring measure.

Background Info—Acuity Type Test Together with Grid Tests:

The purpose of a home vision monitoring test is to enable patients to recognize changes in vision and when there is a change in vision to take help-seeking action to minimize the time between the start/worsening of a vision problem, such as a retina problem, and presentation to an eye care professional. The Amsler Grid is a commonly used home monitoring test that patients can observe and help detect a change in their vision. A near vision acuity test, such as a small font Snellen-like test, can be used in the home. Augmenting a grid test with a secondary test such as a near vision acuity test may provide additional benefit for diagnosing & monitoring retina health as well as diagnosing and monitoring other vision problems.

Providing a reduced-font Snellen-like test for in-home use may have limited ability for the test to yield an absolute (ie: clinically repeatable and accurate) measure of acuity (because of variations in printing size, variations in the space between the eye and the test, inconsistency in use, improper lighting, improper use, etc). However, gaining an absolute measure of acuity is not necessary in order to have a successful monitoring tool. Observing a significant difference from one test (perhaps a baseline test) and another test conducted days/weeks/months in the future provides the user with an ability to compare two readings and look for a relative change between the two vision tests. To the extent that a patient can maintain consistency in their observations, a non-absolute measurement is sufficient to help a patient recognize a change in vision that may need to be brought to the attention of his/her eye care professional.

The Challenge of Near-Vision Acuity Tests in Monitoring

Unfortunately, the success of a patient's ability to evaluate a change in near vision acuity is dependent upon the patient's ability to compare a current reading with a reading taken at an earlier date. Without a facility for documenting a patient's near vision acuity, the patient must rely upon their memory as the means of comparing. The letters offered in a typical near-vision acuity test are offered in a way as to prevent memorization and do not spell a word or offer a pneumonic assistance. And, the label associated with each line of vision is often printed discretely to minimize distraction, which prevents it from being used as an easy tool to help remember one's reading test result.

Consequently, near vision acuity tests such as reduced font Snellen-like tests pose a challenge in implementation for successful use in monitoring vision over time.

DETAILED DESCRIPTION OF THE DRAWINGS

Figure 1:
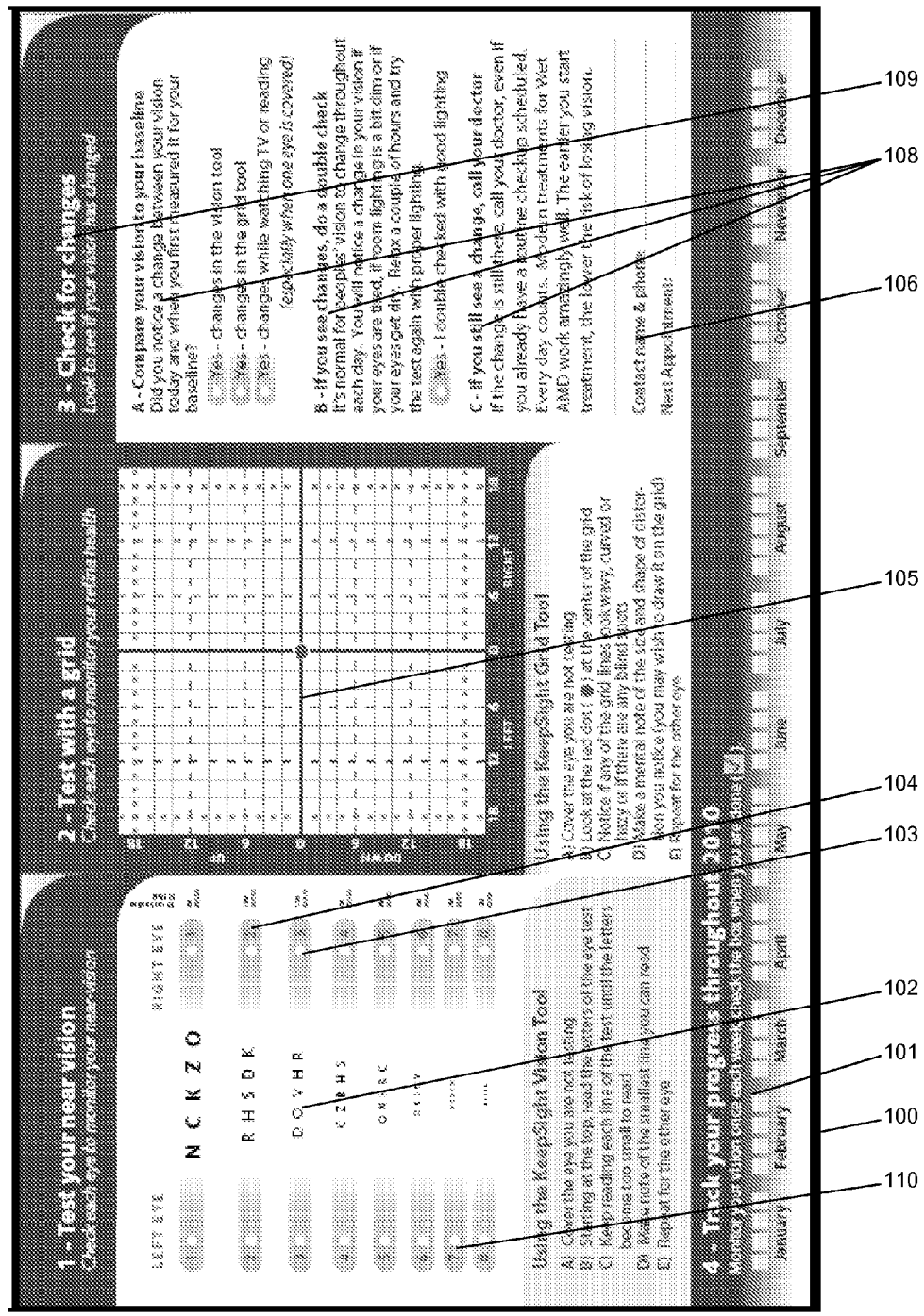
FIG. 1 is a layout view of a printed vision monitoring and diagnostic test system.

FIG. 1 is a layout view of a printed vision monitoring and diagnostic test system.
100—Vision test system
101—Date tracking component
102—Near vision acuity test
103—Right eye writable recording space
104—Character size identifier
105—Grid test
106—Interactive space
108—Action steps
109—Test guidelines
110—Left eye writable recording space Vision test system 100 comprises a plurality of vision tests, including a near vision acuity test 102 and a grid test 105 and a date tracking component 101 together with interactive space 106, action steps 108, and sequential test guidelines 109.

Near vision acuity test 102 includes multiple rows of characters. Each row includes characters of the same basic height. Same sized characters may be selected from a variety of families including capital letters, lower case letters, pictograms, directionally pointing characters, etc. In this example, same sized characters include sample capitalized letters. In this example, sample capitalized letters are used and the capitalized letters are selected from a subset of letters known as EDTRS letters.

Patients may use these same sized characters to determine their near vision acuity. An absolute vision measurement of near vision acuity may be performed using standardized character sizes held at a specific distance between said characters and the user's pupil in proper lighting conditions to provide a clinical diagnosis of acuity. A relative vision measurement of near vision acuity may be performed by a given user using the same type of near vision test on two separate occasions and comparing the results of those two measurements.

Character sizes may be selected to match industry standards, such as Snellen, M-Units, Jaeger, Point Size, LogMar, etc. Such adherence to a given standard facilitates creation of an absolute vision test measurement. Character sizes may be selected that do not reflect a given standard.

Each grouping of characters of the same size is associated with a character size identifier 104. If a character size is printed to match a given standard, then the character size identifier 104 may be printed to reflect the name of the associated size of the given standard, for example "20/20". The character size identifier 104 may also be displayed as a generic identifier as shown in the drawing, such as "1", "2", "3", etc. This enables the patient to not become concerned with the use of such a test as a clinical diagnostic yet still maintain the ability to remember their visual performance over time, thus enabling proper monitoring. The character size identifier 104 may also use picto-grams or icons to enable the patient to remember their visual performance over time, thus enabling proper monitoring. Regardless the nature of the identifier, such as generic or picto-gram, identifiers may be linked to a given standard and a key provided to the eye care specialist, so that the results obtained in a clinical setting may be used as a clinical diagnosis.

Each grouping of characters of the same size includes a right eye writable recording space 103 and a left eye writable recording space 110. The recording spaces provide users with the ability to acknowledge their ability to read the grouping of characters of the same size. If the patient is able to read the grouping of characters of the same size, the writable recording space enables them to acknowledge their performance through a visible marking. In this example, a circular checkbox is provided as the writable recording space and the user is instructed to place a check in the circular check box if the user successfully reads the characters of the same size for that circular check box for the eye being tested. The check written by the user or user's helper is the visible marking Writable recording spaces may comprise a variety of graphic designs that enable people to make a marking, which may comprise a variety of shaped check-boxes, fill-in-the-blank bubbles of various shapes, and various characters that may be circled, said characters including letters, numbers, picto-grams, and other visuals.

Providing right and left eye recording spaces 104, 110 enables users to compare their vision over time and improves the quality of monitoring by reducing dependence upon users' memory and subjective comparison over time. Recording a user's vision at a baseline test date, such as upon the date of an annual vision check, provides an objective reference point to which the user may compare vision weeks and months after the baseline without influence of subjectivity or mental lapse associated with influence of time and memory quality. This improves user confidence.

Application of an identifying check mark to a circular check-box may be performed either by the patient, an eye care specialist, a family member or other caregiver or a combination of these over time. In this way, an eye care specialist may use the near vision acuity test 102 of the vision test system 100 in a clinical environment as a clinical diagnostic, assist with placing identifying marks in the recording spaces 104, 110 and then enable the patient to take the test home to use on a routine basis over time to compare their visual performance against the baseline.

Figure 2:
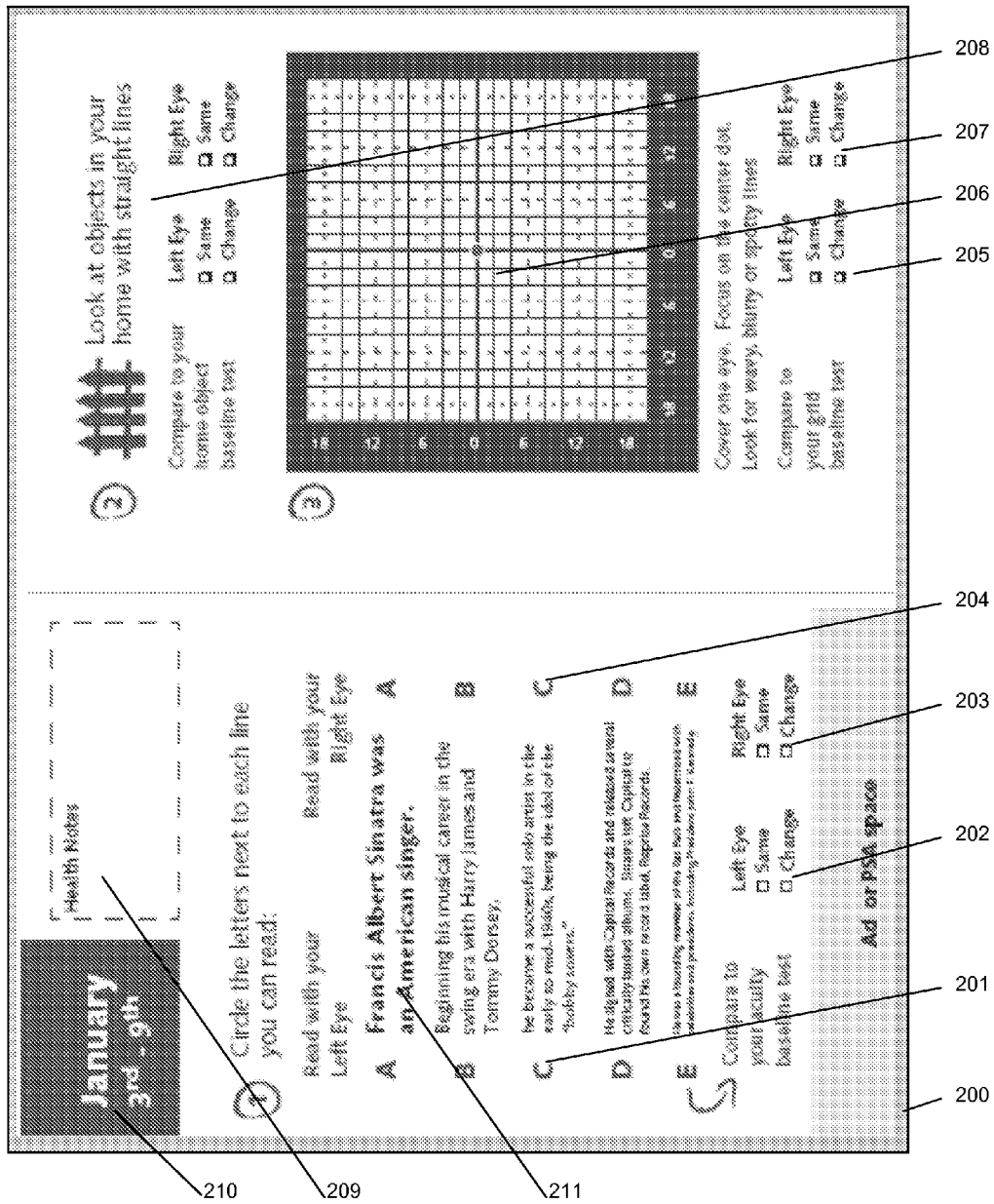
FIGS. 2, 3 and 4 are layout views of pages out of a printed vision monitoring and diagnostic test systems.

FIG. 2 is layout view of pages out of a printed vision monitoring and diagnostic test system.

200—Vision test system
201—Left eye character size identifier and writable recording space
202—Left eye comparison facility
203—Right eye comparison facility
204—Right eye character size identifier and writable recording space
205—Left eye comparison facility
206—Grid test
207—Right eye comparison facility
208—Home object test
209—Note taking space
210—Date tracking component
211—Near vision acuity test Vision test system 200 comprises a plurality of vision tests, including a near vision acuity test 211, a grid test 206, a home object vision test 208 and a date tracking component 210 together with note taking space 209, and sequential test guidelines. Visual test system 200 is envisioned to include multiple pages that provides sufficient number of tests for multiple weeks of vision monitoring.

Near vision acuity test 211 includes multiple rows of characters. In this example, short sentences are used. Patients may use these characters to determine their near vision acuity.

Each grouping of characters of the same size is associated with a right eye character size identifier and writable recording space 204 and left eye character size identifier and writable recording space 201. The recording spaces provide users with the ability to acknowledge their ability to read the grouping of characters of the same size. If the patient is able to read the grouping of characters of the same size, the writable recording space enables them to acknowledge their performance. In this example, the user is instructed to place a circle around the character size identifier and writable recording space 204, 201 if the user successfully reads the associated characters of the same size.

Application of an identifying circle around a writable recording space may be performed either by the patient, an eye care specialist, a family member or other caregiver or a combination of these over time. In this way, an eye care specialist may use one of the near vision acuity tests 211 of the vision test system 200 in a clinical environment as a clinical diagnostic, assist with placing identifying marks in the recording spaces 204, 201 and then enable the patient to take the test home to use on a routine basis over time to compare their visual performance against the baseline. In this example, a collection of test systems 200 would be provided to enable multiple weeks of vision monitoring.

A home objects test 208 provides the user with guidance on how to use objects in their home environment as mechanisms to monitor their vision throughout each day. Home objects with straight lines, such as door jambs, fence posts, Venetian blinds, floor tiles, wall paneling, etc can offer a good tool for detecting a variety of visual distortions. These distortions include wavy lines often associated with edema resulting from onset of neovascularization, macular hole or macular pucker. Blurry lines associated with cataracts, retina problems, diabetic retinopathy, etc. Spotty lines associated with geographic atrophy, neovascularization, etc.

By guiding a user to take notice of a given object or plurality of objects in their home environment, they may establish the appearance of that or those objects upon baseline. They may then compare the appearance of said objects over time to evaluate the progression or onset of vision problems. Any such change in vision may be documented in a writable recording space.

A date tracking component 210 provides the user with a facility to help them remember to use the test on a routine basis and to establish a historical record of patients' vision over time. In this example, a weekly testing routine is taught by the nature of the date tracking component 210. In this example, the weekly date may be pre-printed on the vision test system 200 or may be provided on a sheet of stickers such that the user may place a pre-printed date sticker onto their vision test system 200. The date tracking component may simply provide a writable space to enable the user to write in the date, such as the word "date" followed by a blank line for the user to fill-in.

Comparison facilities are provided for the near vision acuity test 211, grid test 206 and home objects test 208. Examples of left eye comparison facilities are shown as 202 and 205. Examples of right eye comparison facilities are shown as 203 and 207. These comparison facilities enable a user to document the results of their current visual performance as compared against the performance during prior tests at earlier dates. More specifically, the comparison facilities teach users to compare their current test results with the results garnered during a baseline test. This procedure emphasizes the use of the tests over time as a means of objectively monitoring vision.

A section is provided for health notes 209.

Figure 3:
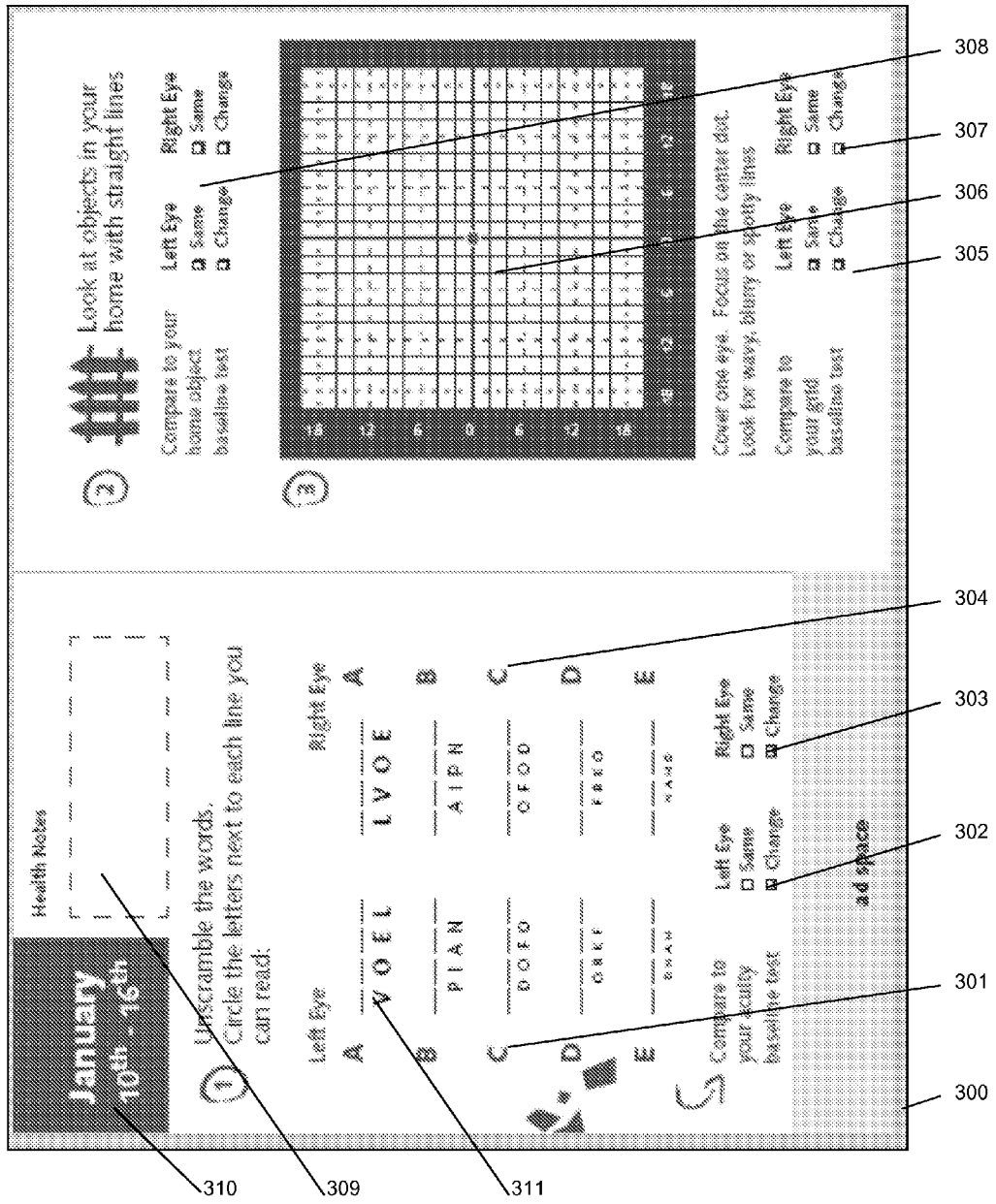

FIG. 3 is layout view of pages out of a printed vision monitoring and diagnostic test system.

300—Vision test system
301—Left eye character size identifier and writable recording space
302—Left eye comparison facility
303—Right eye comparison facility
304—Right eye character size identifier and writable recording space
305—Left eye comparison facility
306—Grid test
307—Right eye comparison facility
308—Home object test
309—Note taking space
310—Date tracking component
311—Near vision acuity test Vision test system 300 comprises a plurality of vision tests, including a near vision acuity test 311, a grid test 306, a home object vision test 308 and a date tracking component 310 together with note taking space 309, and sequential test guidelines. Visual test system 300 is envisioned to include multiple pages that provides sufficient number of tests for multiple weeks of vision monitoring.

Near vision acuity test 311 includes multiple rows of characters. In this example, capitalized letters are used. Patients may use these characters to determine their near vision acuity. In this example, capitalized letters are offered in sets of four associated with common 4 letter words, with their sequence scrambled. In such a way, the user may evaluate their vision and may have the enjoyment of solving a word puzzle. The use of such a puzzle overcomes the potential for boredom associated with a standard near vision acuity eye chart, and can help drive routine use for many years.

The remaining aspects of vision test system 300 are similar in design to vision test 200 and may therefore be used collectively to form a booklet or other aggregation of routine tests.

Figure 4:
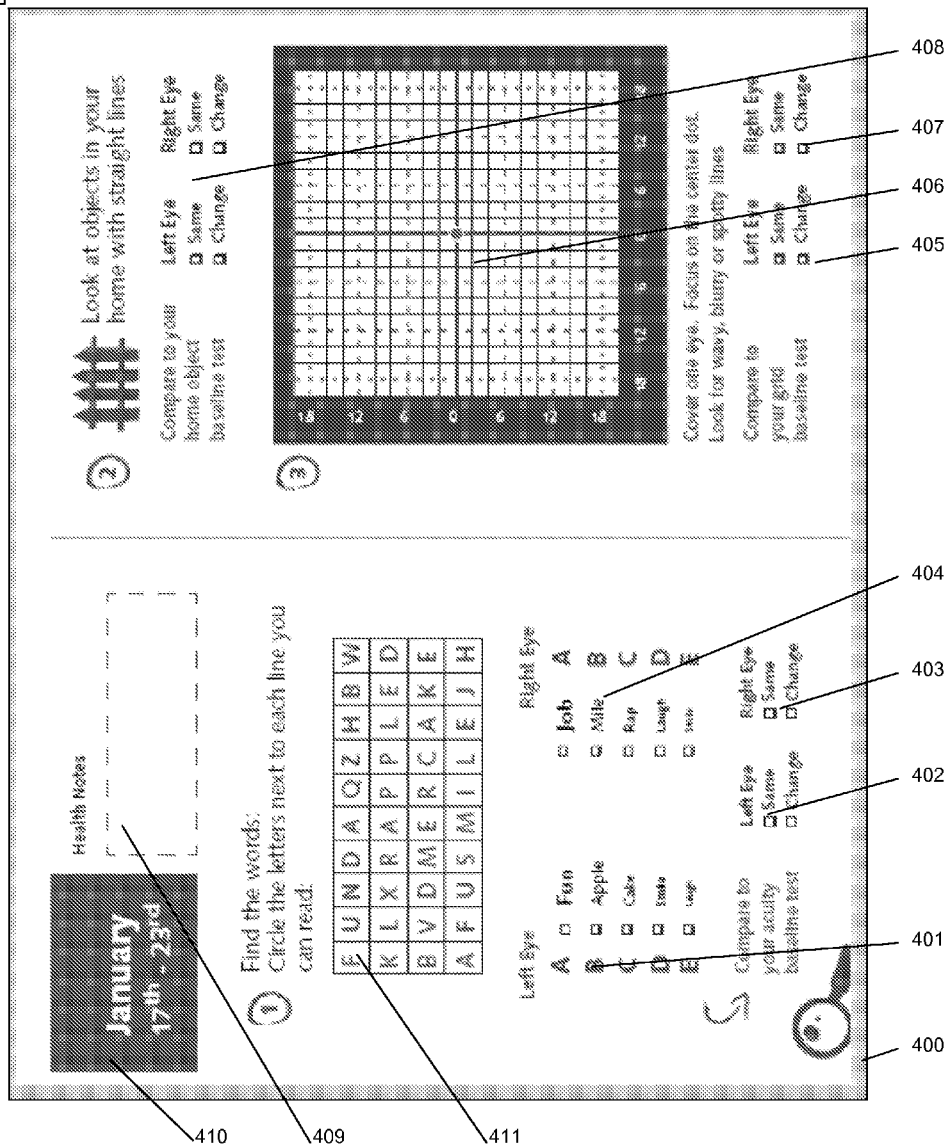

FIG. 4 is layout view of pages out of a printed vision monitoring and diagnostic test system.

400—Vision test system
401—Left eye character size identifier and writable recording space
402—Left eye comparison facility
403—Right eye comparison facility
404—Right eye character size identifier and writable recording space
405—Left eye comparison facility
406—Grid test
407—Right eye comparison facility
408—Home object test
409—Note taking space
410—Date tracking component
411—Word search near vision acuity test Vision test system 400 comprises a plurality of vision tests, including a word search near vision acuity test 411, a grid test 406, a home object vision test 308 and a date tracking component 410 together with note taking space 409, and sequential test guidelines. Visual test system 400 is envisioned to include multiple pages that provide sufficient number of tests for multiple weeks of vision monitoring.

Near vision acuity test 411 includes multiple rows of characters. In this example, letters are offered as common 3, 4 and 5 letter words. A word search feature 411 is provided. In such a way, the user may evaluate their vision and may have the enjoyment of solving a word puzzle. The use of such a puzzle overcomes the potential for boredom associated with a standard near vision acuity eye chart, and can help drive routine use for many years.

The remaining aspects of vision test system 400 are similar in design to vision test system 300 and vision test system 200 may therefore be used collectively to form a booklet or other aggregation of routine tests.

Figure 5:
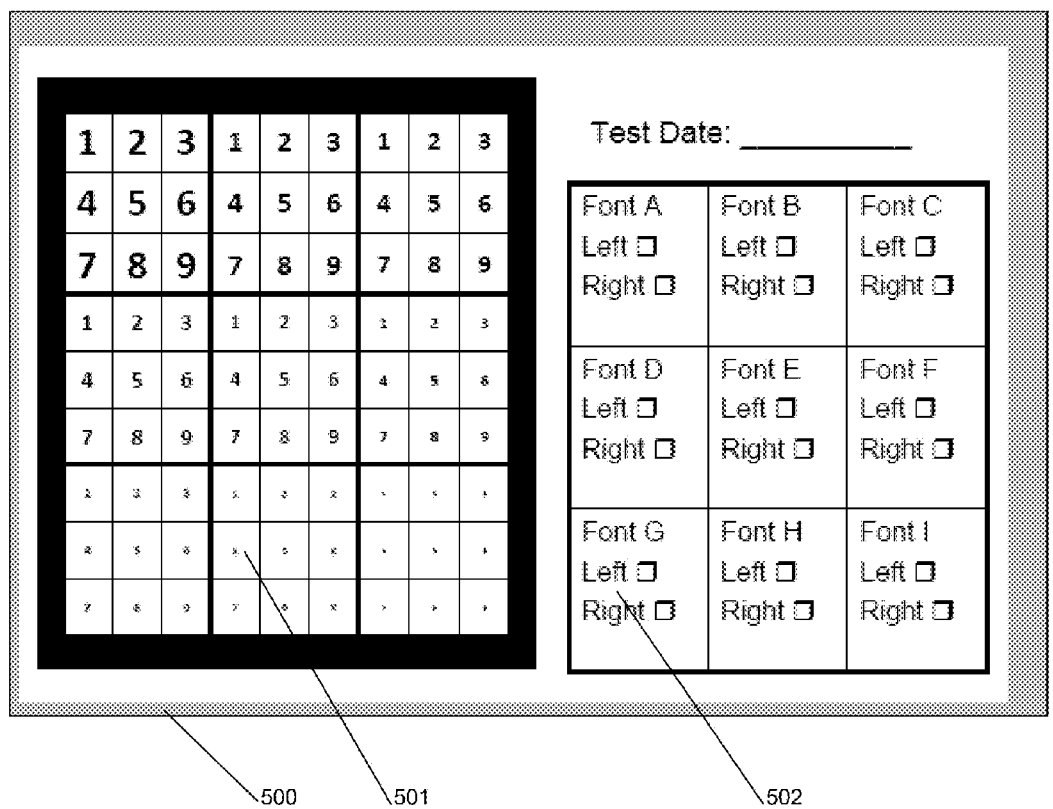
FIGS. 5, 6 and 7 are layout views of game-based vision monitoring and diagnostic test systems.

FIG. 5 is a layout view of game-based near vision acuity monitoring and diagnostic test.

500—Near vision acuity game test
501—Numerical matrix game
502—Writable recording space Near vision acuity game monitoring and diagnostic test 500 enables people to test their near vision acuity while also enjoying a game. Each section of the numerical matrix game 501 uses a distinct character size. Players use a writable recording space 502 to denote which character size they can read, and which they cannot read without aide of a magnifying glass.

In this example, character sizes are changed within each game. Games may also be arranged such that character sizes stay consistent across the game, yet are changed across multiple pages of games. In this way, the user can identify which character size they can read and which they cannot.

Figure 6:
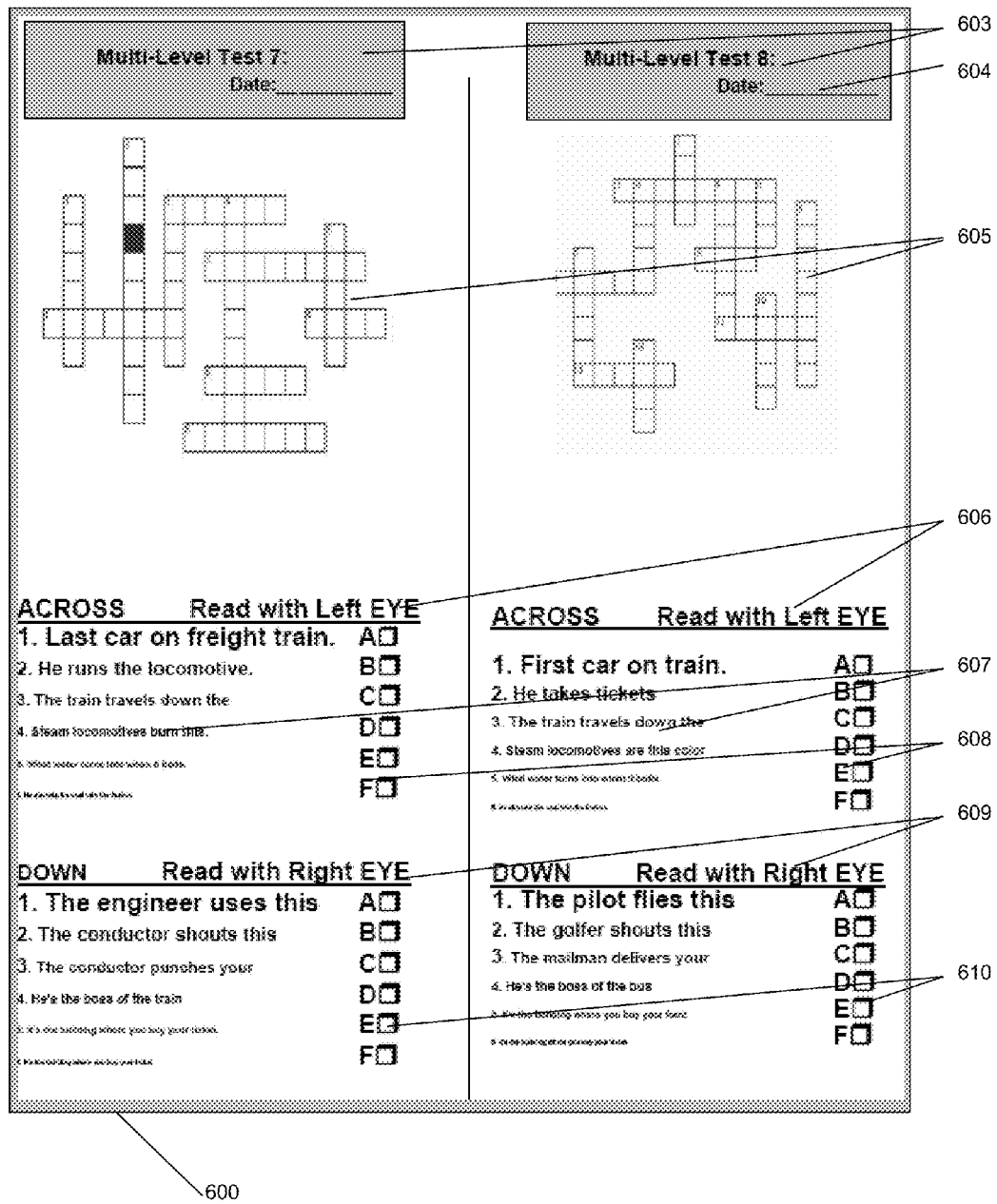

FIG. 6 is a layout view of game-based near vision acuity monitoring and diagnostic test.

600—Near vision acuity game test
603—Test identifier
604—Date tracking component
605—Crossword puzzle game
606—Left eye instructions
607—Common sized characters
608—Character size identifier
609—Right eye instructions
610—Recording spaces Near vision acuity game monitoring and diagnostic test 600 enables people to test their near vision acuity while also enjoying a crossword puzzle game 605. Clues for the crossword puzzle game 605 are offered as a group in the down direction for one eye as identified by left eye instructions 606 and the other eye in the across direction as identified by right eye instructions 609. Each row of clues is offered using common sized characters 607. Each grouping of common sized characters 607 is associated with a character size identifier 608 and recording spaces 610. Players use the recording spaces 610 to denote which sizes they can read, and which they cannot read without aide of a magnifying glass.

In this example, font sizes are changed within each game. Games may also be arranged such that font sizes stay consistent across the game, yet are changed across multiple pages of games. In this way, the user can identify which character size they can read and which they cannot. Results may be compared against a baseline to enable monitoring of near vision acuity over time.

Figure 7:
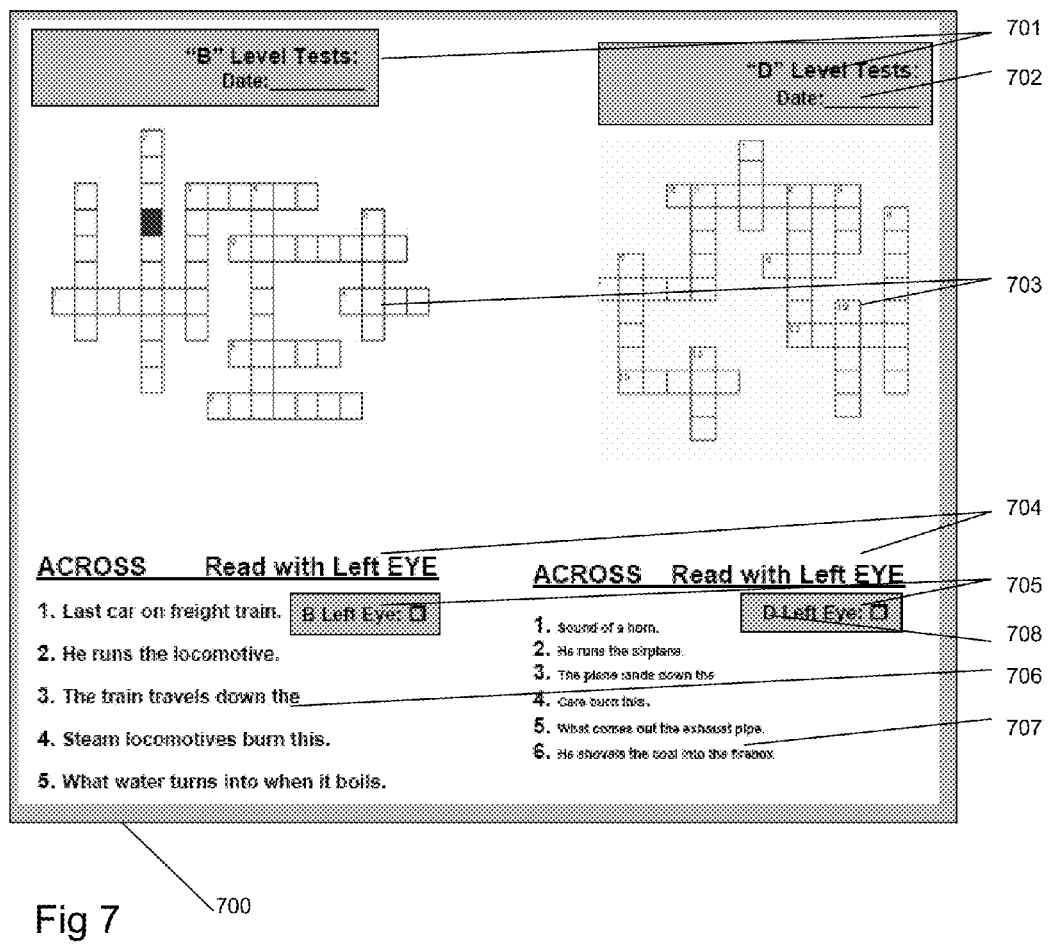

FIG. 7 is a layout view of game-based near vision acuity monitoring and diagnostic test.
700—Near vision acuity game test
701—Test identifier
702—Date tracking component
703—Crossword puzzle game
704—Left eye instructions
705—Recording spaces
706—Common sized characters
707—Common sized characters Near vision acuity game monitoring and diagnostic test 700 enables people to test their near vision acuity while also enjoying a crossword puzzle game 703. Clues for the crossword puzzle game are offered as a group in the down direction for one eye as identified by left eye instructions 704 and the other eye in separate instructions for the across direction. Each set of clues is offered using common sized characters 706 and 707. Each grouping of common sized characters 706 and 707 is associated with a character size identifier 708 and recording spaces 705. Players use the recording spaces 705 to denote which sizes they can read, and which they cannot read.

In this example, font sizes stay the same within each game. Users are offered multiple games to enable them to determine which character size they are capable or reading and playing and which they are not.

Figure 8:
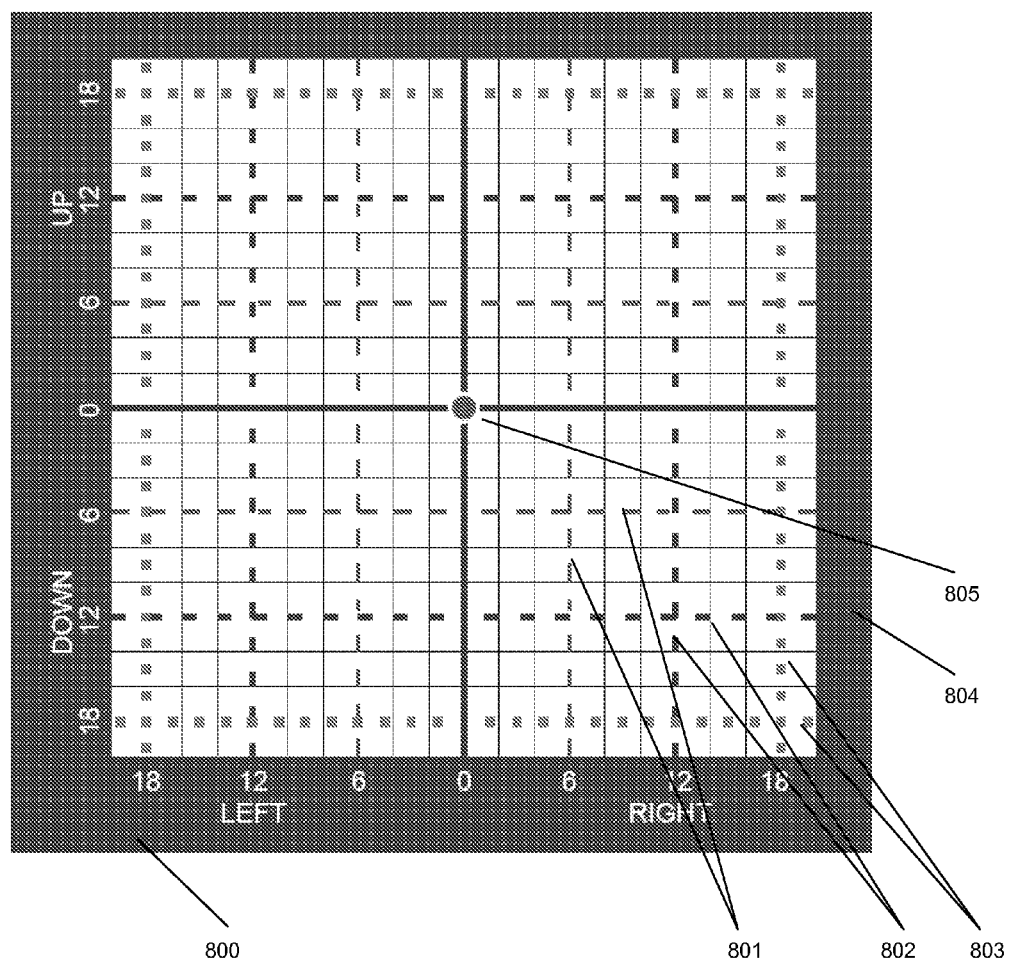
FIG. 8 is a layout view of a grid test for retinal illness.

FIG. 8 is a layout view of a grid test for retinal illness.
800—Grid test
801—Distinguishably different line set 1
802—Distinguishably different line set 2
803—Distinguishably different line set 3
804—Very broad boarder line
805—Center point Grid test 800 shows a variety of features described in an earlier patent. Grid test 800 comprises indicators created by distinguishably different line sets 801, 802, and 803. Each of the distinguishably different line sets 801, 802 and 803 include a pair of horizontal lines and a pair of vertical lines and are symmetric about a center point 805. Distinguishably different line set 801 is the closest of the distinguishably different lines to the center point 805. Distinguishably different line set 802 is next closest of the distinguishably different lines to the center point 805. Distinguishably different line set 803 is the next closest of the distinguishably different lines to the center point 805. The broadness of the lines within the line set increases as their distance from the center dot increases. This increase in line broadness helps compensate for the reduction in near vision visual acuity from central vision into the periphery. Users have an easier capability to detect subtle changes because of the compensating effect of the increasing broadness of the distinguishably different line sets.

In the current example, distinguishably different line set 801 is established at 0.5 mm, distinguishably different line set 802 is established at 1 mm, distinguishably different line set 803 is established at 1.5 mm. Actual broadness of the line sets may vary, but this example shows a working dimension.

The grid test 800 may also be configured to increase the breadth of the outer perimeter line 804 such that it is much wider than the lines that comprise the grid system. This very bold perimeter provides frame around a users central vision. This bold frame is very helpful to patients with advanced retinal damage and who may no longer have the ability to see the center dot of a grid test. Thus, the wide perimeter line is configured to provide ease of stabilizing gaze for patients who lack central vision.

DETAILED DESCRIPTION OF THE INVENTION

Facilitating Home Monitoring with Interactive Hardcopy Visual Acuity Tests:

Home monitoring using near vision acuity and distance acuity requires the patient to acknowledge a change in acuity over time. A straightforward way to monitor for change over time is to establish a baseline result, and then compare further acuity results to the established baseline. Most patients hold reading materials at a fairly consistent distance, and those with corrective lenses often have only a narrow band of distance where they can read. So, there is a natural capability for people to maintain functional consistency in near vision acuity measurements over time.

Use of a documented baseline result provides a method to reduce reliance on short & long-term memory, and thereby increase likelihood of an objective comparison of visual acuity over time. Similarly, the establishment of a baseline and subsequent comparison of other sensory symptoms can also help provide objective comparisons over time in a variety of areas, comprising grid test results, visual appearance of straight lines in the home environment, ability to watch television, and visual acuity at longer non-reading distances.

Including a writable recording space along the side of each row of a reduced-font Snellen-like near vision acuity test, we provide space for the patient to acknowledge their successful or unsuccessful completion of reading that row for a given eye. This writable recording space confers ability for a person to conduct an initial base-line assessment of their vision and easily, clearly and intuitively record the results of that assessment which can then be referred to in further testing as a baseline reference point. For example, a user could place a check-mark as a marking to confirm that he or she successfully read a given line of same-sized characters.

The writable recording space can vary. In one embodiment, if a patient is able to read a specific row of the near vision acuity test with their left eye, they can place a marking in a check-box for the left eye along side that row. This continues for each subsequent row until the patient can no longer read the row. When the patient can no longer read the row, he/she does not place a mark in any further check boxes for that eye. The test is ten repeated for the other eye.

For each test, the patient attempts to read the row with the largest character size, and subsequent rows with smaller character sizes until they can no longer read a row.

Providing available space immediately adjacent to each row is a novel solution. It simplifies the creation of a baseline. It also provides patients a simplified way to compare a recent test result with the baseline result for the same eye. If the patient used a test and could not read a row that had a check-mark in its check-box for the eye being tested, it becomes evident that the patient's vision has changed since the baseline when they marked that check-box. They can then be instructed to take appropriate action (for example, call the eye care professional to discuss).

Writable recording spaces may be conferred by a variety of means comprising, check boxes of various shapes, bubbles to fill-in, characters to circle or underscore or highlight and various other means of marking. Similarly in electronic formats, responses may be captured in a variety of interactive means including radio buttons and various other approaches.

The use of writable recording spaces is also valuable in tracking other visual and sensory performance characteristics, comprising grid tests, monitoring of objects in the home to search for a change in their appearance, distance vision acuity, perimetry, contrast sensitivity, color blindness, eye teaming, eye tracking, depth perception, ability to watch television, ability to read printed materials, use of game-based acuity measures, and others.

Thus, an interactive hardcopy visual acuity test comprises at least one set of same-sized characters printed upon one of a paper, plastic and other semi-rigid substrate, said at least one set of same-sized characters of appropriate size to enable one of a near vision acuity test or a distance vision acuity test, having writable recording spaces to enable a person to apply a marking to make a record of the user's visual acuity performance during the test.

Method of Using the Test for Monitoring Between Eye Care Visits to Accelerate Follow Up Visit when Needed In a preferred embodiment, a variety of vision tests with writable recording spaces is provided by doctors to their patients. Said embodiment also including written and/or pictorial guidance on how to use the tests to establish a baseline assessment of vision and how to compare subsequent vision test results back to the baseline. In a preferred embodiment the baseline is preferably established by the doctor or the doctor's staff using the tests as part of the vision exam, else conducted the same day, or within a week, of a patient's eye exam. Said baseline results are then used as a reference for the intervening time until the next scheduled eye exam. A self-monitoring regimen can be directed by the eye care professional, for example on a weekly basis.

The intention of synchronizing the establishment of the baseline proximal to the patient's eye exam is to provide the eye care professional and patient with a means for monitoring the patient's vision health between office visits, so that in the event of a change in vision, the patient can communicate the change with the doctor, and if appropriate, return for an accelerated visit prior to the routinely scheduled visit. Users would recognize a loss in near vision acuity when they could no longer read a given character size that they had previously acknowledged that they could read (through an indication such as a check mark). The value of a relative vision measurement can also become more meaningful to an eye care professional, if they are aware of an absolute vision measurement established the same day as the relative baseline. In an ideal situation, an eye care professional would be able to listen to a patient's feedback regarding a relative change in vision and use the patient's last clinical measure of absolute vision to gain an approximation of the patient's current visual health. This can be especially valuable in home monitoring situations where it may be difficult for a patient to gain access to a doctor, and a phone based conversation regarding relative change in vision may enable a more confident assessment regarding the need for a patient to make a visit to the doctor, or whether the patient may not require short term presentation.

Combining the Novel Near Vision Acuity Test with Clinical Use

Such a near-vision acuity test could be used by the eye care professional during a routine exam. By ensuring that the character sizes adhere to commonly accepted optometric standards, and knowing the distance between the eye and the test unit, the eye care professional could use the test in the standard exam process for documenting the patient's near vision acuity and recording the results in the patient's chart. Additional to marking the results in the patient's chart, either the eye care professional or the patient could mark each of the writable spaces associated with the character sizes that the patient was able to read during the exam, and thereby complete the baseline process before leaving the eye care professional's office. The patient could then take the test home and use it for routine monitoring.

Interactive Acuity Tests—Paper Based—Through Games and/or Serial Tests

Conducting an acuity test can lose its efficacy if the user memorizes the letters in a Snellen-like test. It can also become boring, leading to a drop in compliance with routine monitoring.

One solution using paper based hardcopy tests is to provide multiple iterations of the acuity test and then alter the content of each discrete test. For example, one week the row associated with 20/20 vision may include the letters "E G T F C" and the following week the same row may include the letters "T R M E F". This prevents memorization of the test, but does not necessarily make it more interesting.

A novel way of making near vision acuity testing more interesting is to incorporate the acuity test into word and/or number games that are already popular with people. For example, a commonly known game is a word scramble. In such a game, the letters of a word are re-sequenced, allowing the user to properly sequence them to reveal the word. For example, a word scramble may present the letters "O L V E", to which the solver could spell the word "LOVE" or "VOLE".

In such a word game, the game could be physically arranged, so that at least one scramble was offered for at least one reference acuity level. At baseline, the user could play the game and evaluate their ability to complete the game based upon their acuity (and independent of their cognitive game play ability). The user could then be offered the same sized test at a later date and be able to compare their reading ability to their baseline reading ability.

In one embodiment, a word scramble game would have 7 word scramble challenges, each challenge set at a specific font size. The font sizes could include 7 of the following: 3, 4, 6, 8, 10, 12, 14, 16, 18 or other sizes as the designer specifies. At least one test could be produced. Multiple tests would have different words for content but adhere to the same font size arrangement.

Adjacent to each line of the word scramble would be a writable space to allow the user to acknowledge whether they could read the test or not. Similar to the check-box near vision acuity test described above, the word scramble near vision acuity test would allow the user to check each box associated with lines that the patient could read. A separate box could be provided for each eye—left and right. This embodiment provides diversity of sizes in close proximity.

In another embodiment, a word scramble game could have various sections, each with its own font size. For example several pages could be set at 3 font, several at 4 font, several at 6 font, several at 8 font, several at 10 font, several at 12 font, several at 14 font, several at 16 font, etc.

The patient could establish a baseline by attempting to perform the game in each of the sections. If the patient could read the games in a section, they would acknowledge their completion with a check-box and/or writing the date. Each game may have writable space adjacent to it to mark the fact that they accomplished that game.

Future tests would reveal whether the patient could successfully complete games offered at each font size. In the event that the patient was unable to read a game that was at a font size that he or she had previously been able to accomplish, it would be a sign of a change in vision. This embodiment would provide a variety of sections each having similar font sizes within said section.

A Variety of Games are Amenable to this Novel Design

A variety of games may be amenable to this novel design. Guidance can be given to test one eye at a time.

Crossword Puzzles.

Crossword puzzles may be laid out in at least two embodiments. In the first embodiment, the totality of word clues could be organized in a way that there were multiple font sizes, with at least one clue for at least two font sizes. In this way, the user would be presented initial clues at a large font and adjacent to this clue or clues would be a check-box to indicate the font size associated with the clue(s). Subsequent clues(s) would be presented in subsequently smaller font sizes. For each font size, there would be a check box to acknowledge successful reading of the clues. In another embodiment, sections of crossword puzzles could be clustered together, each associated with a common font size. Associated with each game would be a check-box or other means of demonstrating reading of the clues. In another embodiment, the same crossword could be offered in two or more font sizes, each game being associated with a check-box that enabled the user to demonstrate their mastery of reading that font size.

Word Search

Word searches provide an opportunity to offer individual games with a variety of fonts for each clue, or multiple games gathered in at least one section, each section containing a common font and each game having a means of acknowledging the reading of the words.

Number Puzzles such as Sudoku

Number games including matrix organization of numbers such as described in Sudoku-type puzzles can offer different numbers in a single game to be at different font sizes or multiple games gathered in common font sized sections. If different fonts were available in one game, a separate key would enable the users to understand the font sizes offered and to acknowledge their reading of each of the font sizes.

Trivia or Reading Games

Questions of trivia can be offered, with multiple choice answers in variable sized fonts. Reading selections can be offered with multiple choice answers available thereafter. Either the reading selection or the questions can be varied in character size.

Game Review:

Games such as crossword, word scramble, number games, word searches, etc can be used to monitor near acuity if organized in a novel manner: By organizing games in such a way, they can be used to assist in routine monitoring. Games offer a unique advantage, as they have the motivational power to engage people's attention, provide diversion and fun, and thereby confer increased likelihood of routine usage.

Games can be organized to include specific character sizes, when users are playing the games, they can then understand if they have historically been able to read a specific character size, and then are no longer able to read it, that this can indicate a change in vision.

One way to arrange games is to have variable character sizes within an individual game. For example by varying the sizes of characters of the clues within the same game. In such a way, at least two font sizes are offered. The clues are then labeled to allow the user to know the size of the font used for the clue that he or she is attempting to read. Writable recording spaces may be offered to facilitate baselining and subsequent comparisons to baseline.

This method is advantageous in that it scans multiple fonts in one game, allowing the user to rapidly assess their vision at a variety of levels. This method has its drawbacks, as it can be frustrating to some users who may be upset at not being able to complete a game because they were not able to read all of the clues.

Yet another way to arrange games is to have a game with a single character size. Character sizes would vary from game to game. In such a way, an entire game would have clues of one character size. In one embodiment, a book may have 60 total games with 10 games at each of 6 font sizes.

In such a book, tests would be labeled to allow the user to know the font size of that particular game's clues. It may also allow a space for the user to check their successful accomplishment or failure and the date of the attempt.

Yet another way to arrange games is through multiple game book offerings. In such a way, at least two or more game books could be offered, each one with only one font size for the clues.

The cover and internal pages of the game book would indicate the size of the clues inside, so that the user could select accordingly. In this way, a user would select the smallest font that they could comfortably read. The user could continue buying that size font book for weeks/months/years knowing that if it became unreadable, that it was a sign of needing to go to the eye doctors' office.

Yet another way to arrange games is to have a game with two or more parallel sets of clues, each set with a different character size.

Yet another embodiment is a hybrid of multiple approaches described above, with the ability to offer multiple books with limited numbers of fonts.

Interactive Date Components Associated with Paper Test

We can also provide space on a vision tests for the patient to interact with the paper test directly (or thru a family member or carer) in an ongoing fashion. Having a tool that enables patients to acknowledge the use of the test, is one way of encouraging interaction. A series of check-boxes associated with weeks of the year, enables patients to conveniently create a mark to signify that they completed their test for that time period. For example, a set of check-boxes adjacent to dates that represent each Sunday of the current year and following year will enable the patient to check the box to acknowledge that they conducted the test at least once that week; or, having pre-printed dates on each page, as is found in a weekly diary; or providing a plurality of dated stickers which may be removed from its roll or sheet and placed upon a page of a diary-like test booklet.

Such interaction also provides a topic of conversation and patient feedback at follow-up office appointments with the eye-care professional. A patient can share their testing history with the eye care professional, who can then use this information to provide counseling or guidance on how to optimize their future testing regimen.

Home Objects Tests

Patients are typically directed to use home vision monitoring tests on a weekly or daily basis. Patients may successfully augment this regimen with ongoing appreciation of their home environment. Many objects in the home may provide significant input to a patient's current visual health status. Objects with straight lines, such as Venetian blinds, wall paneling, ceiling tiles, fence posts, and other objects often provide an excellent tool for monitoring edema of the retina, which creates a wavy appearance of otherwise straight lines. For example, someone with a conversion from dry to wet AMD may notice that the lines of their Venetian blinds become wavy in a section of their vision.

The novel systems herein provides guidance on what home objects should be used for monitoring, the ability to make note of the object selected, guidance on the proper covering of one eye during monitoring, writable recording space to establish baseline observation data regarding whether the selected object was clear, spotty, wavy or blurry, and writable recording space to provide subsequent status, and guidance on how to spot changes in vision between the baseline and subsequent readings.

Grid Tests

Left & Right Grids Displayed as a Pair

Traditional Amsler grids are distributed to retina patients printed on paper or card-stock on a one-per patient basis. Many people fail to cover one eye when testing their vision. This is especially problematic when one suffers from vision loss in the non-dominant eye. A study by Olsen showed that many patients do not present after onset of wet AMD until their vision has deteriorated greatly—often degrading to 20/80 or worse than 20/100. Many people do not present, simply because they never close their dominant eye and view the world through their non-dominant eye alone. It therefore makes sense to provide patients with a pair of grid tests to help encourage proper testing & monitoring of both eyes.

Having two tests on a single piece of paper provides the patient with the ability to capture notes and other information for each eye separately and increase the likelihood of successfully detecting a change in vision over time.

Multiple Grids in Series

By making paper tests available in series, for example in a bound booklet or glue-bound pad or other means, one can provide a user with a means of collecting a history of results, and also maintain one test as a reference point or baseline. For example, a bound booklet of 53 sheets of printed grid tests (described herein) would enable the first test to be conducted with an eye care professional and allow the patient to denote the limits of their affected area, and provide a baseline reference point. (The affected visual area could be drawn as a facsimile on the grid lines of test, described by a rectangle or circle or plurality of rectangles & circles around the affected area(s), noted on check-boxes associated with each line, etc)

Additional tests could then be taken subsequently by the patient on a weekly basis in their home. This would provide weekly monitoring between two annual office visits. The subsequent tests could then be referenced against the initial baseline test and evaluated for a change in vision. This approach to monitoring would be assisted by an interactive way of checking completion of the test. For example, a check-box or calendar indicia (ie: a pre-printed weekly date, for example each Sunday of the year) on each page, to help reinforce the notion of regular testing (in this case weekly). It would also enable the patient to bring the test booklet back with them to the doctor to review the patient's monitoring compliance rate and visual history.

The use of a diary format for routine vision testing is a novel concept. Use of formats such as a weekly diary format confers multiple benefits. It provides the ability to track monitoring over time, it provides a visual feedback if the user does not finish the written aspects of their test, and it provides the ability to mark upcoming health appointments and reduce likelihood of forgetting appointments.

Manual Check-Boxes on a Grid Test

The most straightforward way to monitor for change over time is to establish a singular baseline result, and then compare future results to the baseline.

Patients may accomplish this by attempting to sketch an outline of their affected area(s) on the surface of a grid test. This requires a not insignificant amount of effort and patience. A method that requires less effort and patience can be accomplished by simply marking each of the lines of the grid test that is affected by the retina condition.

To be clear, a patient with a retina condition, when looking at the central dot of a grid test will observe an area of vision that is affected in some way—such as the waviness of lines, blurry lines, curved lines, missing spaces/gaps in lines, etc.

By associating a check-box with each line of the grid test, a patient can place a mark next to any line (horizontal or vertical) that was associated with the affected part(s) of their vision.

For example, having a check box along the right hand side of each horizontal row of the grid test and at the top of each vertical line of the grid test will provide a space to acknowledge disturbance in any line of the grid test. If the patient conducts the test, and then places a mark in each box associated with each line that was affected, this provides a relative rectangular outline of their affected area. The test is repeated for the other eye, using a separate set of check-boxes so that each eye has its own results. These initial results can be considered a base-line result.

For each future test, the patient observes the grid test but does not necessarily make any further markings on the test, rather they compare the then current result with the baseline result. If the patient finds that one of the lines is then currently showing as "affected", but which had not been marked in the initial baseline, it becomes evident that the patient's vision has changed and can then be instructed to take appropriate action (for example, call the eye care professional to discuss).

VMS Grid Test—Increasing Line Width According to Distance from Center

Grid tests typically have lines of identical width. In a recent non-provisional application, a novel grid known as the VMS grid has been taught by the inventor. Said VMS grid is an element of the vision monitoring systems described throughout this application. The novel grid, which utilizes differentiation of some of the lines and other features to improve the sensitivity and specificity as compared to the Amsler can be further improved in its incorporation into the systems herein.

People's acuity is most sensitive in the foveal region associated with central vision. Vision in the periphery is not as sensitive and acuity drops. By providing lines of increasingly heavier width as one emanates from the central dot of the grid test, one can offer the user an improved ability to detect visual disturbances.

Providing a Bold and Wide Margin to the Exterior of the Grid

Grid tests typically are presented as a graph of black ink on white background or vice-versa. The final perimeter line is typically created of a similar line weight as the line weight used for the lines that comprise the grid.

By radically increasing the line weight of the outer perimeter by a factor of 5 or more, the user has a new visual cue that is visible in his or her peripheral vision. Line width of 0.5 inches or more allow the use of this area for display of reversed type of the latitude & longitude markings of the VMS grid.

This strong border line can be of significant benefit, as people with reduced central vision may not easily see the central dot. Many people with central scotomas no longer have functional vision, and therefore cannot see the central dot. This makes it difficult to hold one's vision steady and to stabilize the gaze at the center of the test. By providing a very wide external border line, the user now has a way to better stabilize his or her gaze, even in the absence of seeing the central dot. Use of this external peripheral boundary can denoted as "centerless referencing" as it enables users to stabilize their gaze without needing to see the central dot.

Systems

Organization of Testing Materials into a System—Multiple Tests

Several concepts have been disclosed herein. These can work discretely or together as a holistic system. Having multiple types of tests provides higher likelihood of early detection, as varying patients will have varied results with tests. The benefits of combining multiple test types together into a system can also be realized by the collective feedback providing additional assurance to a patient that a change in vision is real and not imagined. A patient may consider a change in one test result to be of minor importance. But, by offering multiple tests, there is a likelihood that a change in vision perceived in multiple testing formats can elevate the person's sense of urgency and importance in taking action, specifically by calling their eye care professional.

Inclusion of a Baseline Test

A baseline test can be conducted on a single test device and then used for future reference. A baseline test can also be conducted on a series of tests, where one test (typically the first) acts as the baseline, and further tests are compared back to the baseline.

Such a series of tests can be organized in a booklet, a glue top pad or the like. They may also be organized with the baseline being offered as a stand-alone article, and the series of follow-up tests being offered separately.

In one such embodiment, the baseline test may be offered on a semi-rigid cardstock paper tool that is recommended to be maintained in a visible location such as a refrigerator or mirror. The series of tests are then offered to the user as a booklet of weekly tests published on a regular basis (ie: monthly, quarterly or annually).

In another such embodiment, the baseline test may be offered on a semi-rigid cardstock paper tool that is recommended to be maintained in a visible location such as a refrigerator or mirror. The series of tests are then offered to the user through a regular monthly publication, such as popular daily or weekly newspaper(s), magazine(s) or a specialty publication(s) or newsletter(s).

Method

The intentional labeling of game books to deliberately indicate its font size and infer that said labeling can assist the buyer to monitor the health of their vision over time is a novel aspect of this invention. This allows the users to play a game according to their visual ability and then play games of similar font sizes in the future such that when reading is no longer as easy, it can help signal the need to visit the eye doctor.

Further, the intentional guidance to cover or close one eye and view the game with only one eye is further novel aspect of this invention towards the use of established fonts over time to monitor vision.

Further, the intentional guidance to track the date of tests so that a time based comparison can be made is a further novel aspect of this invention towards the use of established fonts over time to monitor vision.

Further, the intentional guidance to establish a baseline reading capability so that a time based comparison can be made is a further novel aspect of this invention towards the use of established fonts over time to monitor vision.

Electronic Versions

Game play can be offered in an interactive electronic setting on computer, internet handheld device etc. User can be offered a clue for a word game at a random font, the user would then adjust the font with an interactive user interface. User could be offered a large font and proceed to minimize the size of the font until no longer readable, or the user could be offered a tiny font and proceed to sequentially enlarge the font until it was legible. In such cases the computer can offer various starting font sizes and various increments in size adjustments and monitor a user's performance. Performance over time can be compared and a change in vision can be alerted when performance has varied from an established baseline. Baseline can be established by statistically averaging the first uses of the system, accounting for learning, but not providing more than 4 weeks of time prior to start of evaluation.

Interactive Components Associated with Paper Grid Test for a Care Giver

Many patients who are at risk for retina disease have an existing relationship with an eye-care professional. Through periodic exams (ie: yearly or every other year), the patient may be diagnosed by the eye-care professional as having a risk of eye disease, such as wet AMD. A paper-based grid test and or near vision acuity test, with specific interactive tools associated with the test on the same piece of paper may enhance the patient's experience and thereby improve the ability of the patient to detect changes in their vision over time and take the necessary steps to present to their eye-care professional as quickly as they are able.

By providing space and written instructions on the test for the eye-care professional or a member of their office team (or other care giver, such as a family member, nurse, social worker, etc) to write on the test and customize it for each patient, we provide an opportunity for the patient to experience care and get helpful information. This interactive space provides an opportunity for a person to person transaction that is differentiated from handing over a stock Amsler test.

Through this person-to-person health transaction, the intrinsic value of the paper test increases. By increasing the value of the test, we have a higher likelihood of it being used successfully. An analogy for this transaction can be made in comparing the sending of a birthday greeting card to another person; if two identical greeting cards are sent, one of which has a personal note and signature, and one of which only holds the pre-printed message, we can assume that the greeting card with the personal note and signature will hold a higher value in the mind of the recipient than the otherwise un-altered card. This higher perceived value may lead to greater willingness to use the tool and stay compliant on their testing protocol.

Space on the test and printed instructions can be created to help guide and instruct an eye-care professional or one of their team (or other person such as nurse, family member, etc) to write items such as (but not limited to): a contact person's name, a contact person's telephone number, a date for the next appointment, desired frequency of testing, the initial test date (aka baseline date), well wishes, other instructions, etc.

The visually stimulating grid system, interactive hardcopy visual acuity test, and test configured to guide the user to monitor objects in their home test configured to provide a set of instructions to enable users to improve specificity by encouraging a second try after a predetermined period of time and under improved lighting. For example, if patients notice a change in vision, they may be instructed to repeat the tests the next morning, or when their eyes are no longer tired. This practice acknowledges that acuity changes throughout the day and can suffer when user's eyes are tired, dry or otherwise fatigued. In a preferred embodiment, the user is given direction to retest their vision the next morning, and if they continue to notice a change in vision, to briefly note their change and call their eye doctor promptly to relate this information. The eye doctor can then make a determination of when the user should be seen for their next exam.

The invention claimed is:

1. An interactive visual acuity test system comprising:
   a. a hardcopy delivery format;
   b. plurality of lines of same sized characters in each said line;
   c. at least one means for recording the results adjacent to the said lines of same sized characters within the test; and
   d. at least one means for tracking and monitoring vision tests over a period of time;
   wherein the said interactive system enables the user to monitor the vision of one or both of the eyes over a period of time.

2. The interactive visual acuity test system as claimed in claim 1, wherein the said characters are selected from the group of but not limited to a variety of families including capital letters, lower case letters, pictograms, icons, directionally pointed characters, or group of letters in the form of sentences and alike.

3. The interactive visual acuity test system as claimed in claim 1, wherein the said test has at least four lines of same-sized characters, each line of said same-sized characters having one means for recording the result for the left eye and one means for recording result for the right eye.

4. The interactive visual acuity test system as claimed in claim 1, wherein the said means for recording results is configured to enable a user to interact with the test and to create at least one marking on said test such that there is a visible acknowledgement of a patient's acuity of one or both eyes.

5. The interactive visual acuity test system as claimed in claim 1, wherein the said means for recording results is configured to be filled-in with a writing instrument by said user; and is at least one member of check boxes of various shapes, bubbles to fill-in, characters to circle, characters to underscore, or characters to highlight.

6. The interactive visual acuity test system as claimed in claim 1, wherein the test further provides each said line of same sized characters with two said means for recording results, one for the patient's left eye, one for the patient's right eye, thus providing a measure of said patient's visual acuity of one or both eyes.

7. The interactive visual acuity test system as claimed in claim 1, wherein the said means for recording results comprises of an alpha, numeric or pictorial based label to identify said line of same-sized characters, and instructions to guide use of the means for recording results to create said marking by one of a circle, x-mark, underscore, highlight and hash-mark.

8. The interactive visual acuity test system as claimed in claim 1, wherein predetermined character sizes and shapes may be associated with the test in accordance with accepted vision measurement standards, and the test configured to permit the user to record the distance between the characters and the user's pupils thereby enabling one to render an absolute vision measurement of visual acuity.

9. The interactive visual acuity test system as claimed in claim 1, wherein even if the character sizes and shapes do not adhere to an accepted vision standard, the character sizes and shapes are configured to enable relative vision measurement of visual acuity, the user monitoring their vision for changes by comparing said relative vision measurements over time.

10. The interactive hardcopy visual acuity test system as claimed in claim 1, wherein the said test is configured to permit the user to measure distance acuity.

11. The interactive visual acuity test system as claimed in claim 1, wherein the said test is configured to permit the user to measure near vision acuity.

12. The interactive visual acuity test system as claimed in claim 6, wherein the near-vision acuity test is combined with user instructions that enable variability of reading distance between three and thirty inches, a change in reading distance providing input to the user to alert them to a change in vision.

13. A vision monitoring system comprising:
   a. at least one visual acuity test;
   b. at least one visually stimulating grid test;
   c. at least one home object test; and
   d. at least one date tracking component;
   wherein, the said system enables the user to monitor the visual and retina health of respective eyes over a period of time and helps in early diagnosis of defect in the same.

14. The vision monitoring system as claimed in claim 13 wherein the said system is configured:
   a. to guide the user to monitor objects in their home and to provide written instructions and result recording sections enabling a baseline observation and a comparison of baseline against subsequent readings;
   b. to guide the user to monitor objects in their home or neighborhood environment with one eye covered at a time; to monitor for disturbances such as one of waviness, blurriness, spotty vision, distortion, and haziness, and to permit the user to acknowledge the presence of such disturbances in a result recording section in the said test;
   c. to encourage and track usage over time, comprising one of calendar check-boxes, dated stickers, and pre-dated diary pages;
   d. to guide users to improve specificity by encouraging a second try after a predetermined period of time and under improved lighting;
   e. to guide the user to communicate with an eye care professional in the event that a change in vision is observed; and
   f. to encourage the user to adhere with routine vision monitoring over time.

15. A method of use of the vision monitoring system as claimed in claim 13, the said system containing at least one vision test for one or both eyes, said method comprising at least one of the following steps:
   a. providing an acuity test with check boxes to facilitate user's ability to record their results;
   b. providing a grid test with guidance on how to record any perceived visual disturbances; and
   c. providing a test to facilitate observation of objects with straight lines in the home and providing guidance in recording any perceived visual disturbances in an eye.

16. The method of use of interactive vision tests as claimed in claim 15 comprising initially guiding a user to establish a baseline vision measurement.

17. The method of use of interactive vision tests as claimed in claim 15 comprising guiding the user to adhere to a routine vision monitoring schedule the test including a date tracking component and configured to permit recording results of a given user for comparing a baseline vision measurement to a later measurement thereby enabling vision monitoring over time.

18. A vision monitoring game comprising one of printed words and numbers configured to enable a user to monitor vision over time comprising:
   a. a game;
   b. at least one set of instructions or clues;
   c. labeling of character size;
   d. writable recording sections in said game; and
   e. means for facilitating monitoring over time, including:
      i. guidance on covering one eye,
      ii. guidance on establishing a baseline,
      iii. facility for comparing further uses of the games back to the initial baseline to evaluate change in vision over time, and
      iv. instruction on calling a medical professional if a change in vision is noted.

19. The vision game as claimed in claim 18, wherein the said character sizes are grouped and organized in at least one of the following ways:
   a. each instance of an interactive game having variety of character sizes, each size being labeled to indicate its size;
   b. each instance of an interactive game having two or more sets of the same clues, the clues being offered at different character sizes, each size being labeled to indicate its size;
   c. a book having one or more sections with multiple games, each game having one character size, each game having facility to record results, and each section with a common character size;
   d. a plurality of books, each book with one common font size; and
   e. a combination of any two of a.-d.

20. A visually stimulating grid system having a plurality of parallel indicators at predetermined distances from a central point, where distinguishably different lines of the indicators increase in line broadness as they increase in distance from the central point, the increasing broadness configured to improve visibility of said lines as acuity drops with distance from the central point.

21. The visually stimulating grid system according to claim 20, wherein the outer perimeter line is much wider than the lines that comprise the grid system, configured to provide ease of stabilizing gaze for patients who lack central vision.

* * * * *